(12) United States Patent
Rao et al.

(10) Patent No.: US 7,893,300 B2
(45) Date of Patent: Feb. 22, 2011

(54) PROCESS FOR THE PREPARATION OF POLYMORPHS OF SELECTIVE SEROTONIN REUPTAKE INHIBITOR

(75) Inventors: Dharmaraj Ramachandra Rao, Maharashtra (IN); Rajendra Narayanrao Kankan, Maharashtra (IN)

(73) Assignee: Cipla Limited, Mumbai (IN)

( * ) Notice: Subject to any disclaimer, the term of this patent is extended or adjusted under 35 U.S.C. 154(b) by 546 days.

(21) Appl. No.: 10/577,714

(22) PCT Filed: Nov. 4, 2004

(86) PCT No.: PCT/GB2004/004672
§ 371 (c)(1), (2), (4) Date: Dec. 18, 2006

(87) PCT Pub. No.: WO2005/047229
PCT Pub. Date: May 26, 2005

(65) Prior Publication Data
US 2007/0135524 A1 Jun. 14, 2007

(30) Foreign Application Priority Data
Nov. 4, 2003 (IN) .................. 1158/MUM/2003

(51) Int. Cl.
*C07C 211/00* (2006.01)
(52) U.S. Cl. .................................... 564/305
(58) Field of Classification Search ............ None
See application file for complete search history.

(56) References Cited

U.S. PATENT DOCUMENTS

| | | | |
|---|---|---|---|
| 4,536,518 A | 8/1985 | Welch, Jr. et al. | |
| 5,248,699 A * | 9/1993 | Sysko et al. | 514/647 |
| 5,734,083 A | 3/1998 | Wilson et al. | |
| 6,452,054 B2 | 9/2002 | Aronhime et al. | |
| 6,495,721 B1 | 12/2002 | Schwartz et al. | |
| 6,500,987 B1 | 12/2002 | Schwartz et al. | |
| 6,517,866 B1 | 2/2003 | Am Ende et al. | |
| 6,600,073 B1 | 7/2003 | Schwartz et al. | |
| 6,858,652 B2 | 2/2005 | Aronhime et al. | |
| 2002/0183555 A1 | 12/2002 | Schwartz et al. | |
| 2003/0055112 A1 | 3/2003 | Schwartz et al. | |

FOREIGN PATENT DOCUMENTS

| | | |
|---|---|---|
| WO | WO 01/32601 A1 | 5/2001 |
| WO | WO 01/45692 A1 | 6/2001 |
| WO | WO 03/093217 A1 | 11/2003 |

OTHER PUBLICATIONS

International Search Report and Written Opinion, PCT/GB2004/004672, May 17, 2005, 14 pgs.
International Preliminary Report on Patentability, PCT/GB2004/004672, May 17, 2005, 11 pgs.
Haleblian, John K., et al., "Characterization of Habits and Crystalline Modification of Solids and Their Pharmaceutical Applications," Journal of Pharmaceutical Sciences, vol. 64. No. 8, Aug. 1975, pp. 1269-1288.
Almarsson, Örn, et al., "High-Throughput Surveys of Crystal Form Diversity of Highly Polymorphic Pharmaceutical Compounds," XP-002295000, American Chemical Society, Crystal Growth & Design, vol. 3, No. 6, 2003, pp. 927-933.
Remenar, Julius F., et al., "Salt Selection and Simultaneous Polymorphism Assessment via High-Throughput Crystallization: The Case of Sertraline," American Chemical Society, Organic Process Research & Development, vol. 7, No. 6, 2003, pp. 990-996.

* cited by examiner

*Primary Examiner*—Daniel M Sullivan
*Assistant Examiner*—Clinton Brooks
(74) *Attorney, Agent, or Firm*—Conley Rose, P.C.; Rodney B. Carroll

(57) ABSTRACT

The present invention is directed to Form II, III, IV and V of sertraline hydrochloride and methods for its preparation. According to the present invention, the various polymorphs of sertraline hydrochloride may be produced either, directly from sertraline base or sertraline acetate.

4 Claims, No Drawings

PROCESS FOR THE PREPARATION OF POLYMORPHS OF SELECTIVE SEROTONIN REUPTAKE INHIBITOR

CROSS-REFERENCE TO RELATED APPLICATIONS

This application is a filing under 35 U.S.C. 371 of International Application No. PCT/GB2004/004672 filed Nov. 4, 2004, entitled "Process For The Preparation Of Polymorphs Of Selective Serotonin Reuptake Inhibitor," claiming priority of Indian Patent Application 1158/MUM/2003 filed Nov. 4, 2003, which applications are incorporated by reference herein in their entirety.

FIELD OF THE INVENTION

The present invention relates to a process to manufacture various crystalline polymorphic forms of sertraline hydrochloride from either sertraline base or sertraline acetate. The process is rugged and suitable for large scale manufacture of various forms of sertraline hydrochloride namely, Form II, Form III, Form IV and Form V.

BACKGROUND OF THE INVENTION

Sertraline hydrochloride, (1S-cis)-4-(3,4 dichlorophenl)-1,2,3,4-tetrahydro-N-methyl-1-naphthalenamine hydrochloride, having the formula 1 is approved, under the trademark Zoloft® by the US Food and Drug Administration, for the treatment of depression, obsessive-compulsive disorder and panic disorder.

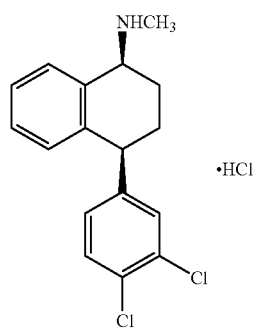

Formula 1

U.S. Pat. No. 4,536,518 ("the '518 patent") describes the preparation of sertraline hydrochloride with a melting point of 243-245° C. by treating an ethyl acetate/ether solution of the free base with gaseous hydrogen chloride. The solid state properties of the sertraline hydrochloride so produced are not otherwise disclosed.

U.S. Pat. No. 5,734,083 describes the preparation of a form of sertraline hydrochloride denominated polymorph "T1".

According to U.S. Pat. No. 5,248,699 ("the "699 patent"), the sertraline hydrochloride produced by the method of the '518 patent has a crystalline form denominated "Form II" The '699 patent discloses four other polymorphs of sertraline hydrochloride designated Forms I, III, IV, and V, and characterizes them by single crystal x-ray analysis, powder x-ray diffraction, infra-red spectroscopy, and differential scanning calorimetry. The '699 patent reports that Form II is produced by rapid crystallization of sertraline hydrochloride from an organic solvent, including isopropyl alcohol, ethyl acetate or hexane, and generally describes methods for making sertraline hydrochloride Forms I-V. According to this patent, the preferential formation of Forms I, II or IV in an acidic solution consisting of isopropyl alcohol, hexane, acetone, methyl isobutyl ketone, glacial acetic acid or, preferably, ethyl acetate, depends on the rapidity of crystallization. The only method described in this patent for making Forms II and IV is by the rapid crystallization of sertraline hydrochloride from an organic solvent such as those listed above.

U.S. Pat. No. 6,452,054 describes novel polymorphic Forms XI, XII, XIII, XIV, XV and XVI of sertraline hydrochloride, processes for preparing them, methods of using them to treat disease, methods of using them to make other sertraline hydrochloride forms, and to pharmaceutical dosages containing the novel forms.

U.S. Pat. No. 6,495,721 discloses novel methods to make Form II of sertraline hydrochloride. Sertraline hydrochloride Form II may be produced directly from sertraline base or sertraline mandelate. It may also be produced from sertraline hydrochloride.

U.S. Pat. No. 6,500,987 is directed to Forms II, III, V, VI, VII, VIII, IX and X of sertraline hydrochloride and novel methods for their preparation.

U.S. Pat. No. 6,600,073 describes novel methods for the preparation of sertraline hydrochloride Forms III, V, VI, VII, VIII, IX and X.

United States Patent Application 0020183555 relates to a process for making sertraline hydrochloride Form II comprising the steps of dissolving sertraline base or sertraline mandelate in an organic solvent to form a solution, adding hydrogen chloride to the solution, heating the solution to a temperature between about room temperature and about reflux for a time sufficient to induce the formation of sertraline hydrochloride Form II; and isolating sertraline hydrochloride Form II.

US patent application 20030023117 describes new and novel polymorphic Forms XI, XII, XIII, XIV, XV and XVI of sertraline hydrochloride, processes for preparing and methods of using them to treat disease, methods of using them to make other sertraline hydrochloride Forms and to pharmaceutical dosages containing the novel forms.

US patent application 20030055112 describes Forms II, III, V, VI, VII, VIII IX and X of sertraline hydrochloride and novel methods for their preparation. According to the present invention, sertraline hydrochloride polymorph II may be produced by slurrying sertraline hydrochloride polymorph VI in an aprotic organic solvent. Sertraline hydrochloride polymorphic Form III may be produced by heating sertraline hydrochloride polymorphs V and VI. Sertraline hydrochloride Forms V and VI may be produced from either sertraline hydrochloride or sertraline base by crystallization. Sertraline hydrochloride Form VII may be produced by suspending sertraline chloride polymorph V in water, followed by filtration. Sertraline hydrochloride Forms VIII and IX may be produced by suspending sertraline base in water followed by acidification and filtration. Sertraline hydrochloride Form X may be produced by suspending sertraline hydrochloride in benzyl alcohol with heating, followed by filtration.

U.S. Pat. No. 6,517,866 deals with various salts of sertraline such as sertraline asparate, sertraline acetate, sertraline lactate and sustained release dosage forms thereof.

SUMMARY OF THE INVENTION

The present invention relates to a process for making sertraline hydrochloride polymorphs Form II, Form III, Form IV and Form V.

The present invention further relates to a novel and cost effective process for making sertraline hydrochloride Form II, Form III, Form IV and Form V, comprising the steps of treating sertraline acetate in suitable solvents with hydrogen chloride gas to give either Form II, Form III or Form IV depending on the solvent and temperature.

The present still further relates to a process for making a sertraline hydrochloride Form V comprising the steps of dissolving sertraline base in acetic acid and treating with hydrochloric acid and isolating sertraline hydrochloride Form V.

DETAILED DESCRIPTION OF THE INVENTION

The present invention provides new processes for making sertraline hydrochloride from sertraline acetate. Sertraline acetate is prepared as per the process described in U.S. Pat. No. 6,517,866 from sertraline base.

Sertraline base is dissolved in a suitable solvent. Suitable solvents includes ethyl acetate, toluene, acetone, 1-methylbutyl ether, hexane and cyclohexane, and mixtures therefore. The pH of the sertraline base solution is lowered by the addition of glacial acetic acid to precipitate sertraline acetate. The most preferred solvents are n-hexane and toluene.

In a preferred embodiment of the present invention, sertraline acetate is suspended/dissolved in suitable solvents and hydrogen chloride is added to convert the sertraline acetate into sertraline hydrochloride.

Hydrogen chloride used may be added as a gas or a solution with an organic solvent, such as a solution of isopropyl alcohol and hydrogen chloride, n-butanol and hydrogen chloride, acetone and hydrogen chloride, or the like.

In another preferred embodiment of this invention to make Form II of sertraline hydrochloride, sertraline acetate is suspended/dissolved in suitable solvents such as isopropanol, toluene, methanol, ethanol, ethyl acetate or mixtures thereof at ambient to elevated temperatures ranging from 30° C. to 80° C., hydrogen chloride is added to adjust the pH of the reaction mixture to between 1 to 2. The addition of hydrogen chloride to sertraline acetate in suitable solvents is exothermic and the temperature rises from ambient to 60° C.-65° C. The mixture is then cooled gradually to ambient with no external cooling provided over a few hours. The product may be cooled over this period from 60° C.-65° C. to 25° C.-20° C. The product so obtained is isolated and dried at about 80° C. under vacuum to give sertraline hydrochloride Form II. The cooling time is typically in the range 2 to 6 hours, but it may be outside this range (eg above this range), depending on the size of the batch.

The most preferred solvent for making sertraline hydrochloride Form II is a mixture of isopropanol and toluene. The solvents are preferably taken in ratios ranging from 1% to 95% toluene. The more preferred ratio being in the range of 2-8% toluene. The most preferred ratio being 3%-5% of toluene in isopropanol.

In another preferred embodiment of this invention to make sertraline hydrochloride Form III, sertraline acetate is suspended/dissolved in suitable solvents such as isopropanol, toluene, methanol, ethanol, ethyl acetate or mixtures thereof at ambient to elevated temperatures ranging, from 30° C. to 80° C., hydrogen chloride is added to adjust the pH of the reactant mixture to between 1 to 2. The addition of hydrogen chloride to sertraline acetate in suitable solvents is exothermic and the temperature rises from ambient to 60° C.-65° C. The mixture is then cooled rapidly with aid of an ice bath and the temperature is brought down to 15° C. to 18° C. within 15 minutes. The product so obtained is isolated by filtration and dried at about 80° C. under vacuum to give sertraline hydrochloride Form III. The cooling of the mixture to produce Form III may be carried out to bring the temperature to 15° C. to 25° C., preferably 15° C. to 20° C. The cooling time may be less than 30 minutes, less than 15 minutes, or from 15 to 30 minutes.

The most preferred solvent for making sertraline hydrochloride Form III is a mixture of isopropanol and toluene. The solvents are preferably taken in ratios ranging from 1% to 95% toluene. The more preferred ratio being in the range of 2-8% toluene. The most preferred ratio being 3%-5% of toluene in isopropanol.

In another preferred embodiment of this invention to make sertraline hydrochloride Form IV, sertraline acetate is suspended/dissolved in suitable solvents such as isopropanol, toluene, methanol, ethanol, ethyl acetate or mixtures thereof at ambient to elevated temperatures ranging from 30° C. to 80° C., hydrogen chloride is added to adjust the pH of the reaction mixture to between 1 to 2. The addition of hydrogen chloride to sertraline acetate in suitable solvents is exothermic and the temperature rises from ambient to 60° C.-65° C. The mixture is then cooled rapidly with the aid of an ice bath and the temperature is brought down to 15° C. to 18° C. within 30 minutes. The product so obtained is isolated and dried at 60° C. in a fluid bed drier to give sertraline hydrochloride Form IV. The cooling of the mixture to produce Form IV may be carried out to bring the temperature to 15° C. to 25° C., preferably 15° C. to 20° C. The cooling time may be from 30 minutes to 1 hour, or less than 30 minutes.

The most preferred solvent for making sertraline hydrochloride Form IV is isopropanol. Preferably, the solvent used for making sertraline hydrochloride Form IV does not include toluene.

In another preferred embodiment of this invention to make sertraline hydrochloride Form V, sertraline acetate is suspended/dissolved in water and hydrochloric acid is added to adjust the pH of the reaction mixture to between 1 to 2. The mixture is stirred at about 25° C. for 2 hours. The product so obtained is isolated and dried at 60° C. under vacuum to give sertraline hydrochloride Form V.

In another preferred embodiment of this invention to make sertraline hydrochloride Form V, sertraline base is dissolved in acetic acid. Water is added as a diluent and aqueous hydrogen chloride is added to adjust the pH of the reaction mixture to between 1 to 2. After precipitation of the products the reaction is further diluted with water before isolation of the product. The product so obtained is isolated and dried at 65° C. in a fluid bed drier to give sertraline hydrochloride Form V.

In this specification the term "ambient temperature" preferably means temperatures from 20 to 35° C.

EXAMPLES

The following examples describe the process of the invention, and are in no way limiting to the scope of the invention.

Reference Examples

Preparation of Sertraline Acetate 30 gms of sertraline base is dissolved in 200 ml of toluene under stirring at room temp. 5 ml acetic acid is added to the clear toluene solution and stirred for 1 hr. at 25° C. to obtain a thick white precipitate. The solids are filtered and re-slurried in 100 ml toluene for 30 minutes and filtered. The product is dried under vacuum at 60° C. for 5-6 hours to give sertraline acetate.

Preparation of Sertraline Acetate 71 gms of sertraline base is dissolved in 350 ml of n-hexane under stirring at room temperature. 14 ml acetic acid is added to the clear solution and stirred for 10 minutes at 25° C. and refluxed at 60° C. for 30 minutes to obtain a thick white precipitate. The precipitated solid is filtered. The product is dried in a fluid bed dryer at 60° C. for 3-4 hours to give sertraline acetate.

Example 1

Preparation of Sertraline Hydrochloride Form II 20 grams of sertraline acetate is suspended in a mixture of 100 ml of isopropyl alcohol and 4 ml toluene. The mixture is heated to 50° C. to get a clear solution and dry hydrogen chloride gas is bubbled to adjust the pH between 1 to 2. The reaction is exothermic and the temperature rises to 60° C. The reaction mixture was cooled gradually to room temperature. The precipitated solids are filtered and washed with isopropyl alcohol and dried under vacuum at 80° C. for 4-5 hours to give sertraline hydrochloride Form II.

Example 2

Preparation of Sertraline Hydrochloride Form III 20 grams of sertraline acetate is suspended in a mixture of 100 ml of isopropyl alcohol and 4 ml toluene. The mixture is heated to 50° C. to get a clear solution and dry hydrogen chloride gas is bubbled to adjust the pH between 1 to 2. The reaction is exothermic and the temperature rises to 60° C. The reaction mixture was cooled rapidly to 15° C. to 20° C. within 15-20 minutes with an ice bath. The precipitated solids are filtered and washed with isopropyl alcohol and dried under vacuum at 80° C. for 4-5 hours to give sertraline hydrochloride Form III.

Example 3

Preparation of Sertraline Hydrochloride Form IV 50 gms of sertraline acetate is suspended in 250 ml of isopropyl alcohol at room temperature. The mixture is heated to 50° C. to get a clear solution and dry hydrogen chloride gas is bubbled to reduce the pH between 1-2. The reaction mixture is cooled to 15-20° C. within 30 minutes under stirring. The precipitated solids is filtered and washed with isopropyl alcohol and dried in a fluid bed drier at 60° C. for 4-5 hour to give sertraline hydrochloride Form IV.

Example 4

Preparation of Sertraline Hydrochloride Form V 10 gms of sertraline acetate is dissolved in 100 ml of water at room temperature under stirring. The solution is filtered to obtain a clear solution. To the clear filtrate 5 ml concentrated hydrochloric acid is added drop wise under stirring to adjust pH between 1 to 2. The precipitated solids are stirred for 1 hour at 25° C. and filtered. The solids are dried under vacuum at 60° C. for 8 hours to give sertraline hydrochloride Form V.

Example 5

Preparation of Sertraline Hydrochloride Form V from Sertraline Base 300 gms of sertraline base is dissolved in 600 ml acetic acid at room temperature and stirred to obtain a clear solution. To the above clear solution, 3000 ml water is added under stirring in 20 min at 25° C. The reaction mixture is cooled to 5°-10° C. and stirred for 1 hr. Concentrated hydrochloric acid is added to the above clear solution and the pH adjusted to between 1 to 2 at 5-10° C. The reaction mixture is stirred for 15 minutes and the sertraline hydrochloride precipitates during this period. 600 ml of water is charged and the reaction mixture is stirred at 10-15° C., for 1 hour. The solids are filtered and dried in a fluid bed dryer at 60-70° C. for 4-5 hrs to give Form V of sertraline hydrochloride Form V of sertraline hydrochloride.

Example 6

Preparation of Sertraline Hydrochloride Formulation

Sertraline hydrochloride (Form II) and Microcrystalline cellulose were cosifted to form premix A. The Premix A was mixed with Starch and Sodium starch glycolate. This was granulated using a starch paste was formed by using starch and purified water. The granules so obtained were then lubricated using microcrystalline cellulose and Magnesium stearate. The lubricated granules were then compressed to form tablets. The tablets so formed were then film coated using a film coating prepared by dispersing Opadry Green 04F51279 and Purified water.

The composition is shown in the following table:

| SR. No. | INGREDIENTS | 25 mg/tab strength |
|---|---|---|
| | INTRAGRANULAR | |
| 1. | Sertraline hydrochloride (Form II) | 27.98 |
| 2. | Microcrystalline cellulose | 29.77 |
| 3. | Starch | 7.50 |
| 4. | Sodium starch glycolate | 4.00 |
| | BINDER | |
| 5. | Starch | 2.50 |
| 6. | Purified water | q.s. |
| | LUBRICANT | |
| 7. | Microcrystalline cellulose | 7.50 |
| 8. | Magnesium stearate | 0.75 |
| | FILM COATING | |
| 9. | Opadry Green 04F51279 | 2.00 |
| 10. | Purified water | q.s. |

Example 7

Preparation of Sertraline Hydrochloride Formulation

Sertraline hydrochloride (Form II) and Microcrystalline cellulose were cosifted to form premix A. The Premix A was mixed with Starch and Sodium starch glycolate. This was granulated using a starch paste was formed by using starch and purified water. The granules so obtained were then lubricated using microcrystalline cellulose and Magnesium stearate. The lubricated granules were then compressed to form tablets. The tablets so formed were then film coated using a film coating prepared by dispersing Opadry Blue 04F50603 and Purified water.

The composition is shown in the following table:

| SR. No. | INGREDIENTS | 50 mg/tab strength |
|---|---|---|
| | INTRAGRANULAR | |
| 1. | Sertraline hydrochloride (Form II) | 55.96 |
| 2. | Microcrystalline cellulose | 59.54 |
| 3. | Starch | 15.00 |
| 4. | Sodium starch glycolate | 8.00 |
| | BINDER | |
| 5. | Starch | 5.00 |
| 6. | Purified water | q.s. |
| | LUBRICANT | |
| 7. | Microcrystalline cellulose | 15.00 |
| 8. | Magnesium stearate | 1.5 |
| | FILM COATING | |
| 9. | Opadry Blue 04F50603 | 4.00 |
| 10. | Purified water | q.s. |

Example 8

Preparation of Sertraline Hydrochloride Formulation

Sertraline hydrochloride (Form II) and Microcrystalline cellulose were cosifted to form premix A. The Premix A was mixed with Starch and Sodium starch glycolate. This was granulated using a starch paste was formed by using starch and purified water. The granules so obtained were then lubricated using microcrystalline cellulose and Magnesium stearate. The lubricated granules were then compressed to form tablets. The tablets so formed were then film coated using a film coating prepared by dispersing Opadry Yellow 04F52565 and Purified water.

The composition is shown in the following table:

| SR. No. | INGREDIENTS | 100 mg/tab Strength |
|---|---|---|
| | INTRAGRANULAR | |
| 1. | Sertraline hydrochloride (Form II) | 111.92 |
| 2. | Microcrystalline cellulose | 119.08 |
| 3. | Starch | 30.00 |
| 4. | Sodium starch glycolate | 16.00 |
| | BINDER | |
| 5. | Starch | 10.00 |
| 6. | Purified water | q.s. |
| | LUBRICANT | |
| 7. | Microcrystalline cellulose | 30.00 |
| 8. | Magnesium stearate | 3.00 |
| | FILM COATING | |
| 9. | Opadry Yellow 04F52565 | 8.00 |
| 10. | Purified water | q.s. |

It will be appreciated that the invention described above may be modified.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

The invention claimed is:

1. A process for the preparation of sertraline hydrochloride Form V consisting essentially of:
   a. suspending/dissolving sertraline acetate in suitable solvents to form a mixture;
   b. adjusting the pH of said mixture to a value of from 1 to 2 with aqueous hydrogen chloride at a temperature of about 25° C.;
   c. stirring the mixture produced in step (b) at about 25° C.; and
   d. isolating and drying under vacuum to obtain sertraline hydrochloride Form V.

2. A process according to claim 1, wherein the sertraline acetate is suspended/dissolved in a solvent selected from the group consisting of methanol, ethanol, isopropanol, ethyl acetate, water and mixtures thereof.

3. A process according to claim 2, wherein the solvent used is water.

4. A process for the preparation of sertraline hydrochloride Form V consisting essentially of:
   a. suspending/dissolving sertraline base in acetic acid to form a mixture;
   b. adjusting the pH of said mixture to a value from 1 to 2 with aqueous hydrogen chloride;
   c. cooling the mixture produced in step (b) gradually to bring the temperature from 30° C. to 5° C.-0° C.; and
   d. isolating and drying the sertraline hydrochloride to obtain Form V.

* * * * *